United States Patent [19]

Hydes et al.

[11] 4,250,189

[45] Feb. 10, 1981

[54] COMPOSITIONS CONTAINING PLATINUM

[75] Inventors: Paul D. Hydes; David M. Watkins, both of Reading, England

[73] Assignee: Johnson, Matthey & Co., Limited, London, England

[21] Appl. No.: 31,876

[22] Filed: Apr. 18, 1979

[30] Foreign Application Priority Data

Apr. 20, 1978 [GB] United Kingdom ............... 15660/78
May 26, 1978 [GB] United Kingdom ............... 22968/78

[51] Int. Cl.$^3$ ...................... A01N 55/02; A61K 31/28
[52] U.S. Cl. .................................. 424/287; 260/429 R
[58] Field of Search ..................... 260/429 R; 424/287

[56] References Cited

U.S. PATENT DOCUMENTS

| 4,115,418 | 9/1978 | Gale et al. | 260/429 R |
| 4,119,653 | 10/1978 | Tobe et al. | 260/429 R |
| 4,119,654 | 10/1978 | Tobe et al. | 260/429 R |
| 4,137,248 | 1/1979 | Gale et al. | 260/429 R |
| 4,140,707 | 2/1979 | Cleare et al. | 260/429 R |

OTHER PUBLICATIONS

Cleare et al., Bioinorganic Chemistry, vol. 2, pp. 202–206, (1973).
Meischen et al., J. Natl. Cancer Inst., 57 (4), pp. 841–845, (1976).
Swartz et al., Cancer Treat. Rep. 61, 1519–1525, (1977).
Leh et al., J. of Pharmaceutical Sciences, 65 (3), pp. 319, 320 & 322, (1976).
Connors et al., Plat. Coord. Complexes in Cancer Chemotherapy, Springer-Verlag, N.Y., p. 135 (1974).
Cleare et al., Platinum Metal Rev. 17, pp. 2 to 13, (1973).
Belluco, Organometallic & Coordination Chemistry of Plat. Academic Press, N.Y., pp. 25, 28, 29, 30, 67, 87, 553, 556, 561, 569 & 570, (1974).

Primary Examiner—Helen M. S. Sneed
Attorney, Agent, or Firm—Cushman, Darby & Cushman

[57] ABSTRACT

This invention relates to platinum co-ordination compounds, to pharmaceutical compositions containing them.

Examples of compositions falling within the scope of the present invention include:

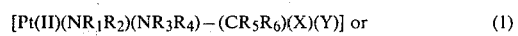

$$[Pt(II)(NR_1R_2)(NR_3R_4)-(CR_5R_6)(X)(Y)] \text{ or} \qquad (1)$$

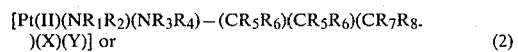

$$[Pt(II)(NR_1R_2)(NR_3R_4)-(CR_5R_6)(CR_5R_6)(CR_7R_8)(X)(Y)] \text{ or} \qquad (2)$$

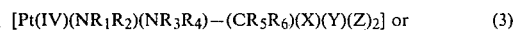

$$[Pt(IV)(NR_1R_2)(NR_3R_4)-(CR_5R_6)(X)(Y)(Z)_2] \text{ or} \qquad (3)$$

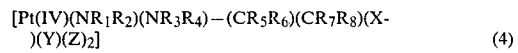

$$[Pt(IV)(NR_1R_2)(NR_3R_4)-(CR_5R_6)(CR_7R_8)(X)(Y)(Z)_2] \qquad (4)$$

the R groups may be the same or different and are selected from H, straight-or branched-chain alkyl, aryl, alkaryl, aralkyl, alkenyl, cydoalkyl, cycloalkenyl, halogen, pseudohalogen (as hereinafter defined), hydroxy, alkoxy, aryloxy, formyl, nitro, amido, amino, sulphonic acids or salts thereof and carboxlic esters, acids and salts thereof, or, two R groups may together represent oxygen or sulphur, and X and Y are the same or different ligands and are selected from sulphate, phosphate, nitrate, carboxylate, substituted carboxylate and water and where R is not H or straight-chain alkyl, additionally halogen or pseudohalogen, and Z is halogen, or pseudohalogen or hydroxy.

3 Claims, No Drawings

COMPOSITIONS CONTAINING PLATINUM

This invention relates to platinum co-ordinate compounds, to pharmaceutical compositions containing them.

According to a first aspect of the invention, a composition of matter comprises a co-ordination compound of platinum having the formula $$[Pt(II)(NR_1R_2)(NR_3R_4) - (CR_5R_6)(X)(Y)] \text{ or} \quad (1)$$

$$[Pt(II)(NR_1R_2)(NR_3R_4) - (CR_5R_6)(CR_7R_8)(X)(Y)] - \text{or} \quad (2)$$

$$[Pt(IV)(NR_1R_2)(NR_3R_4)(CR_5R_6)(X)(Y)(Z)_2], \text{ or} \quad (3)$$

$$[Pt(IV)(NR_1R_2)(NR_3R_4) - (CR_5R_6)(CR_7R_8)(X)(Y)(Z)_2] \quad (4)$$

in which the R groups may be the same or different and are selected from H, straight- or branched-chain alkyl, aryl, alkaryl, aralkyl, alkenyl, cycloalkyl, cycloalkenyl, halogen, pseudohalogen (as hereinafter defined), hydroxy, alkoxy, aryloxy, formyl, nitro, amido, amino, sulphonic acids or salts thereof and carboxylic esters, acids and salts thereof, or, two R groups may together represent oxygen or sulphur;

X and Y are the same or different ligands and are selected from sulphate, phosphate, nitrate, carboxylate, substituted carboxylate and water and, where R is not H or straight-chain alkyl, additionally halogen or pseudohalogen, and Z is halogen, or pseudohalogen or hydroxy.

When Z is absent, the composition of matter is a co-ordination complex of platinum (II) and has the structure:

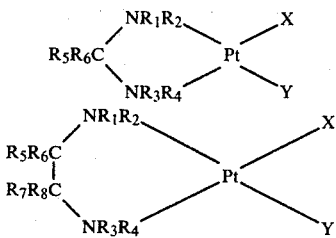

When the Z groups are present, the composition is a coordination complex of platinum (IV) having the structure:

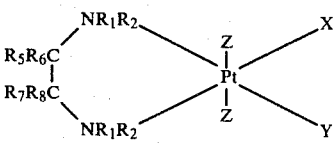

Where X and/or Y is represented by carboxylate or substituted carboxylate, the general formula of which is $C_xR^1_{2x+1}CO_2^-$, we prefer that x is an integer from 1 to 9 inclusive and that the $R^1$ groups are the same or different and are selected from hydrogen, substituted or unsubstituted straight- or branched-chain alkyl, aryl, alkaryl, aralkyl, alkenyl, cycloalkyl and cycloalkenyl, halogen, pseudohalogen (as hereinafter defined), hydroxy, formyl, nitro, amido, amino and sulphonic acid salts. We intend the above definition also to include oxygen and sulphur, such that one doubly-bonded oxygen or sulphur is represented by two $R^1$ groups.

Where X and Y are both carboxylate, they can together comprise a dicarboxylate bidentate ligand, for example oxalate and ligands having the general formula $$-OOC-(CR_y^2R_z^3)_{n^1}-COO^-$$

where $n^1$ is an integer from 2 to 6, $R^2$ and $R^3$ are the same or different and are selected from H, lower alkyl, aryl, alkaryl, aralkyl, alkenyl, cycloalkyl, cycloalkenyl, alkoxy, OH, halogen, pseudohalogen (as hereinafter defined)

or are combined with the carbon atoms to form a cycloalkyl or cycloalkenyl or aryl group and substituted derivatives thereof, and y and z are either 0 or 1 as long as (y+z) is equal 1 or 2.

Suitable dicarboxylate ligands are the succinato, glutarato (pentanedioato), adipato (hexanedioato), pimelato (heptanedioato), malato (cis-butenedioato) and phthalato (o-benzenedicarboxylate) ligands and these may be either substituted or unsubstituted.

The term "pseudohalogen" in this specification has the meaning given on p. 560 of "Advanced Inorganic Chemistry" by Cotton and Wilkinson, Interscience Publishers, 1966, as being "a molecule consisting of more than two electronegative atoms which, in the free state, resembles the halogens; these pseudohalogens give rise to anions which resemble the halide ions in behaviour". Examples of suitable pseudohalogens are cyanide, cyanate, thiocyanate and azide.

Normally the compound is used in association with a pharmaceutically acceptable carrier therefor. Accordingly, in a second aspect, the present invention provides a pharmaceutical composition which comprises a compound according to the first aspect of the invention and a pharmaceutically-acceptable carrier for said compound; these compositions can be formulated so as to be suitable, for example, for parenteral or oral administration.

Preparation details of complexes of platinum according to the invention will now be described by way of example.

PREPARATION OF AQUOSULPHATO (N,N'-DIETHYLETHYLENEDIAMINE) PLATINUM (II)

$K_2PtCl_4$(50 g) in 500 ml water was filtered then KI(79 g) in 150 ml water added with stirring. N,N'-diethylethylenediamine (30 g =37.5 ml) were added. The precipitated diiodo (N,N'-diethylethylenediamine) platinum (II) was filtered off and dried in vacuo (55 g 81%). $PtI_2(Et_2En)$ (25 g) was added to a solution of silver sulphate (13.75 g) in 200 ml of water and stirred at 50° C. for three hours. The supernatant was tested to confirm that no excess silver was present, the silver iodide removed by filtration and the pale yellow liquor freeze-dried to give aquosulphato (N,N'-diethylethylenediamine) platinum (II) monohydrate.

| Assay | Pt | C | H | N | S | O |
|---|---|---|---|---|---|---|
| Calculated | 44.03 | 16.25 | 4.51 | 6.32 | 7.22 | 21.67 |

| Assay | Pt | C | H | N | S | O |
|---|---|---|---|---|---|---|
| Found | — | 16.05 | 4.53 | 6.35 | — | — |

PREPARATION OF BIS(CHLOROACETATO)(N-ETHYLETHYLENEDIAMINE) PLATINUM (II) Pt(ClCH$_2$CO$_2$)$_2$(N-ET EN) (N-ET EN=N-ETHYLETHYLENEDIAMINE)

PtI$_2$(N-ET en) was prepared by Dhara's method using a 10% excess of amine. The product was washed with water (3×100 ml) and ethanol and dried in vacuo at 50° C.

Yield=157.1 g (94.6%)

PtI$_2$(N-Et en) (50 g, 0.093 mol) was added portionwise to a stirred solution of silver nitrate (31.3 g, 0.184 mol) in water at 40° C. and in the absence of light.

The mixture was stirred at 40° C. for three hours, treated with charcoal and filtered through a porosity four sinter. The yellow filtrate was found to be free from excess silver on testing with NaCl.

Chloroacetic acid (19.4 g, 0.205 mol) was added to a stirred solution of the N-ethylethylenediamine diaquo complex (0.92 mol). The solution was adjusted to pH 5–6 with potassium hydroxide, and then warmed to give a pale yellow precipitate. The mixture was stirred overnight and the solid filtered off, washed with water (20 ml), ethanol (25 ml) and dried in vacuo at 60° C. for four hours.

Crude yield=35.0 g (80%)

The crude product was recrystallized from 600 ml of boiling water.

Yield of recrystallized product=20.4 g

| Assay: | Pt | C | H | N | O | Cl |
|---|---|---|---|---|---|---|
| Calculated % | 41.5 | 20.4 | 3.4 | 6.0 | 13.6 | 15.1 |
| Found % | — | 19.7 | 3.5 | 5.9 | — | — |

Further compositions according to the invention include those where all the R groups are H, for example: bis (acetato)(ethylene diamine) Pt (II), aquosulphato (ethylenediamine) Pt (II) and transdihydroxy aquochloracetato (ethylenediamine)Pt(IV), those where R$_1$ to R$_4$ are carboxylate, for example, aquosulphato - N,N,N',N'-tetraacetatoethylenediamine Pt(II) and aquophosphato-N,N,N'N'-tetraacetato ethylene diamine Pt(II), and those where one of the R$_1$ and R$_4$ groups is an aryl group, for example: bis(chloroacetato)-N-phenethylenediamine (Pt(II). Furthermore, an example of a compound where X and Y are halogen is: bis-chloro(N,N,N',N'-tetracetato ethylene diamine) Pt(II).

We claim:

1. A coordination complex of platinum having the formula:

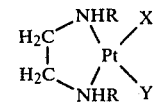

in which the R groups are the same or different and are selected from H and lower alkyl and X and Y are the same or different ligands selected from sulphate, phosphate, nitrate, acetate, chloroacetate and water, provided that X and Y are not both water, such that the platinum is present as Pt(II).

2. A pharmaceutical composition comprising an effective amount of a compound according to claim 1 in combination with a pharmaceutically acceptable carrier.

3. A compound selected from the group consisting of aquosulphato(N,N'-diethylethylenediamine)platinum (II) and bis(chloroacetato)-(N-ethylethylenediamine)-platinum (II).

* * * * *